(12) United States Patent
Carroll, Jr. et al.

(10) Patent No.: US 6,999,167 B2
(45) Date of Patent: Feb. 14, 2006

(54) AUTOMATED REACTOR ENDPOINTING OF PLATY INTERFERENCE EFFECT PIGMENTS

(75) Inventors: James B. Carroll, Jr., Cortlandt Manor, NY (US); Charles Willard, Peekskill, NY (US)

(73) Assignee: Engelhard Corporation, Iselin, NJ (US)

( * ) Notice: Subject to any disclaimer, the term of this patent is extended or adjusted under 35 U.S.C. 154(b) by 671 days.

(21) Appl. No.: 09/782,089

(22) Filed: Feb. 12, 2001

(65) Prior Publication Data

US 2002/0109842 A1 Aug. 15, 2002

(51) Int. Cl.
*G01J 3/42* (2006.01)
(52) U.S. Cl. ............................. 356/319; 356/326
(58) Field of Classification Search ............ 356/319, 356/326, 328, 402, 407
See application file for complete search history.

(56) References Cited

U.S. PATENT DOCUMENTS

| | | | | |
|---|---|---|---|---|
| 4,181,853 A | * | 1/1980 | Abu-Shumays et al. | 250/304 |
| 4,203,670 A | * | 5/1980 | Bromberg | 356/367 |
| 4,403,866 A | * | 9/1983 | Falcoff et al. | 366/132 |
| 4,572,672 A | * | 2/1986 | Orchard et al. | 356/446 |
| 4,978,394 A | | 12/1990 | Ostertag et al. | |
| 5,231,472 A | * | 7/1993 | Marcus et al. | 356/402 |
| 5,563,707 A | * | 10/1996 | Prass et al. | 356/361 |
| 5,793,485 A | * | 8/1998 | Gourley | 356/318 |
| 5,929,998 A | * | 7/1999 | Kettler et al. | 356/405 |
| 5,942,754 A | * | 8/1999 | Yamaguchi et al. | 250/339.12 |
| 6,165,260 A | | 12/2000 | Gale | |
| 6,195,443 B1 | * | 2/2001 | Hammond et al. | 382/100 |
| 6,241,858 B1 | * | 6/2001 | Phillips et al. | 204/192.15 |
| 6,249,751 B1 | * | 6/2001 | Asaba et al. | 356/326 |
| 6,539,325 B1 | * | 3/2003 | Numata et al. | 702/127 |

FOREIGN PATENT DOCUMENTS

| EP | 0 919 599 A2 | 6/1999 |
|---|---|---|
| EP | 0 919 599 A3 | 12/1999 |

* cited by examiner

*Primary Examiner*—Daniel StCyr
(74) *Attorney, Agent, or Firm*—Melanie L. Brown

(57) ABSTRACT

An apparatus and a method for objectively ascertaining a color match between a selected standard color and the color exhibited by an interference effect pigment during processing thereof and terminating the process upon achieving a match. The invention provides a spectrophotometer attached to a flow cell to monitor the color of a platy effect pigment to monitor pigment color and ascertain completion of the coating reaction process involved in interference pigment production.

5 Claims, 2 Drawing Sheets

AUTOMATED REACTOR ENDPOINTING OF PLATY INTERFERENCE EFFECT PIGMENTS

BACKGROUND OF THE INVENTION

Producers of colored products and dispersions seek to achieve a consistent color of their products using many techniques. One simple method involves halting a pigmentation process, applying a coat of the material to a surface and comparing the dried coat to a standard. This method is imprecise and susceptible to unpredictable or untimely production.

Other methods involve evaluating a liquid during the pigmentation process. For example, one method includes directing a portion of a dispersion through a flow cell. One technique provides for observing an illuminated dispersion flowing through the flow cell for comparison with a standard. Another technique directs light through the dispersion in the flow cell onto a spectrometer which compares the characteristics of the light received with specified characteristics.

The known methods are inappropriate for use in connection with production of pearlescent or “effect” interference pigments. Such pigments based on platy substrates which have been coated with a metal oxide layer are well known. These pigments exhibit pearl-like luster as a result of reflection and refraction of light. Depending on the thickness of the metal oxide layer, they can also exhibit interference color effects.

Commercially, the pearlescent pigments encountered most often are the titanium dioxide-coated mica pearlescent pigments and the iron oxide-coated mica pearlescent pigments. They are made by forming a hydrous layer(s) on the substrate and then calcining the composite. The color of the hydrous and calcined layers need not be identical. The color generated is a function of the optical thickness of the coating, which in turn is a function of the refractive index of the coating and the physical thickness of the coating. The physical thickness is a function of the coating process and its parameters and conditions.

Control of the product characteristics is complicated by the fact that free particles of the coating, unattached to a platy substrate, can form and effect the apparent color and also because the color changes rapidly as a result of high reaction rates. To use known methods of color monitoring, therefore, the manufacturing process must be halted, a sample of the in-process material obtained and dried (and also calcined if the end product is intended to be calcined), and then the resulting color characteristics must be compared to a standard. This is clearly not optimal.

To accurately monitor color, it would be necessary to obtain and dry a sample of the pigment, suspend it in a coating carrier and coat a color evaluation substrate before evaluating the color. This also is clearly impractical and time consuming. Typically, therefore, interference effect pigment processing involves a simple subjective visual observation of pigment dispersion as the hydrous coating is being formed on the substrate and maintaining the processing conditions as close to predetermined parameters as practical.

What is needed is an apparatus and a method for objectively ascertaining a color match between a selected standard color and the color exhibited by an interference effect pigment dispersion during processing thereof to allow terminating the process upon achieving a match.

SUMMARY OF THE INVENTION

The invention overcomes the disadvantages noted above by providing an apparatus for controlling the color of an interference effect pigment dispersion during processing using a flow cell, adapted to receive a pigment dispersion, interfaced with a goniospectrophotometer, for measuring a characteristic of the pigment dispersion. The invention controls the color of an interference effect pigment dispersion during its preparation by evaluating light reflected off of the pigment dispersion in a flow cell with respect to a standard.

A method for controlling color of an interference effect pigment during its preparation is provided in which there is a flow cell with a sample of the pigment being formed, light is impinged on the sample, and a characteristic of light reflected from the pigment is compared with a standard. The processing may be terminated when the characteristic corresponds with the standard. The characteristic may be a characteristic of an interference effect of light reflected from the pigment, such as wavelength, dominant wavelength, color space parameters or a combination thereof.

The sample may be mica coated with a high refractive index material.

The invention provides for significantly increasing color-matched pigment output by reducing in-process testing times. The invention provides for reducing inter-batch variability by removing subjective evaluation. The invention provides for reducing lost time and money occasioned by poor product quality. The invention provides for maintaining color consistency, especially with respect to colors of differing intensities and the presence of free coating particles, which make traditional methods of color matching difficult due to interference or subjectivity. The invention provides for matching colors of interference pigments which change rapidly due to high reaction rates, which otherwise would be easy to miss. The invention provides improved elements and arrangements thereof, for the purposes described, which are inexpensive, dependable and effective in accomplishing intended purposes of the invention.

BRIEF DESCRIPTION OF THE DRAWINGS

The invention is described in detail below with reference to the following figures, throughout which similar reference characters denote corresponding features consistently, wherein:

FIG. 1 is a schematic view of an embodiment constructed according to principles of the invention; and FIG. 2 is a graphical representation of spectra of samples processed according to principles of the invention.

DESCRIPTION OF PREFERRED EMBODIMENTS

The invention is an apparatus and a method for objectively ascertaining a color match between a selected standard color and the color exhibited by an interference effect pigment slurry during processing thereof and terminating the process upon achieving a match. The invention includes a flow cell that receives a pigment dispersion stream from a recirculating reaction flask or reactor in which the slurry or dispersion is produced. A spectrophotometer is attached to the flow cell, for measuring a characteristic of the pigment dispersion. Appropriate computer hardware, running appropriate software, is connected to the spectrophotometer for monitoring the interference color of a platy effect pigment and ascertain completion of the coating reaction process involved in interference pigment production. The invention provides a spectrophotometer attached to a flow cell to monitor the interference color of a platy effect pigment as it is being formed and to ascertain completion of the coating reaction process involved in interference pigment production. Specifically, the invention provides for evaluating interference-induced shades and hues that are the reflective coloration of the pigment.

Figure 1:
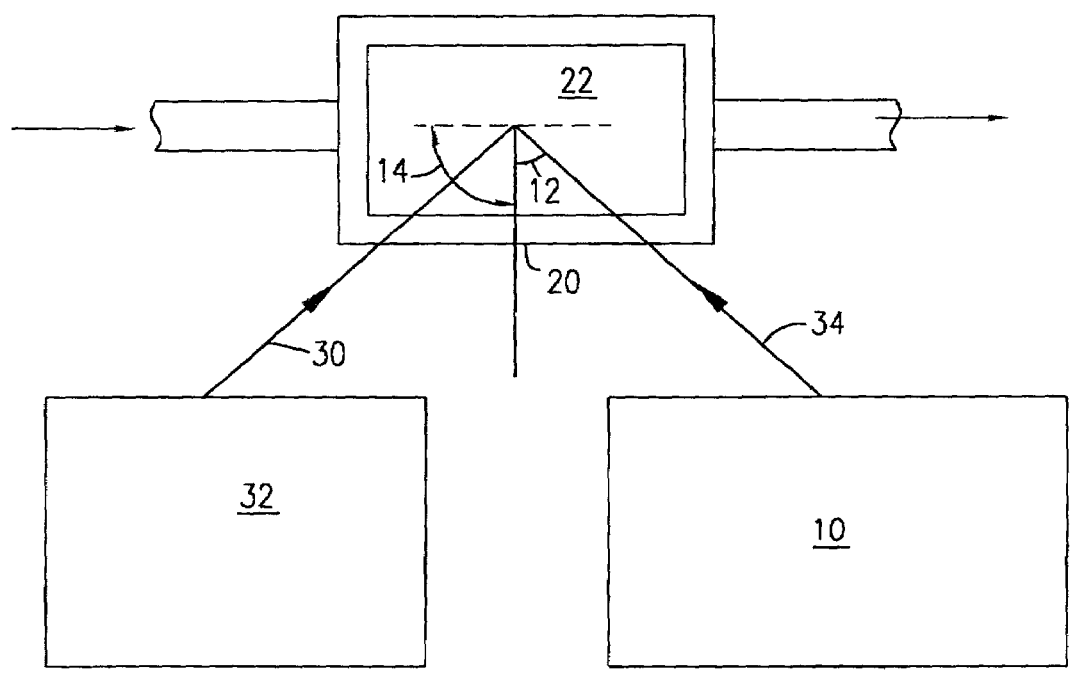

Referring to FIG. 1, the invention includes a flow cell 20 which is connected to a reaction flask or reactor (not shown) in which a pigment slurry or dispersion is created. The reaction flask or reactor continually receives reactants and other materials that alter the characteristics of the pigment dispersion circulating therein. The flow cell 20 receives a stream of the pigment dispersion from the reaction flask or reactor (not shown) as it is produced. The flow cell 20 is positioned to receive a stream of pigment dispersion that is representative of the characteristics of the pigment in the reaction flask or reactor. Thus, measured characteristics of the portion of pigment dispersion in the flow cell correspond closely to characteristics of the pigment dispersion in the reaction flask or reactor.

Referring to FIG. 1, the invention includes, preferably, a goniospectro-photometer 10 capable of measuring at an angle 12 comparable or close to the specular angle 14, which is highly sensitive to the interference color of a pigment dispersion. Preferably, the invention employs a goniospectrophotometer which is sensitive at an angle 12 that is less than or equal to 25° from the specular angle 14.

The goniospectrophotometer 10 monitors the pigment color of a pigment dispersion 22 flowing through the flow cell 20 during development and discerns, in real time, pigment color and appearance. This reduces "holding time," the time in which a pigment dispersion is held during evaluation and prior to completion.

Conventional processing typically occasions significant holding times because of multiple, distinct, time-consuming steps associated therewith. Conventional processing involves obtaining, filtering and calcining a sample. The resultant lacquer-suspended pigment is drawn down over a paper card at a standard thickness. Following drying, the interference effects of the sample are compared with a standard with human or machine vision. The present invention eliminates these time consuming steps as well as the inevitable delays which occur in the real-world execution of the conventional processing steps.

In addition to reducing holding time, the invention also provides for an objective evaluation of the product color. As a result, the present automated pigment process reduces reactor time, requires less rework, produces fewer rejected batches, and yields a more consistent color control.

The flow cell 20 employed by the invention allows the monitoring of the pigment color of a pigment slurry or dispersion 22 flowing therethrough during development and indicates, in real time, pigment color and appearance. This reduces time conventionally necessary to evaluate the product as it is being produced. The flow cell 20 also provides an objective evaluation of the product color. As a result, flow cell pigment processing reduces reactor time, requires less rework, produces fewer rejected batches, and yields a more consistent color control.

The flow cell 20 is configured such that a pigment dispersion 22 flowing through the flow cell 20, and/or platelets of effect colorant therein, is/are oriented relative to the face of the flow cell 20 so as to intensify the interference color. This is accomplished by the use of a thin layer cell, that promotes flow that is parallel to the window face of flow cell 20. Thin flow cells have been typically used in other applications for transmissive color measurement. Interference pigments typically have a thickness on the order of a few microns. To avoid clogs, yet assure appropriate orientation, of pigment in the flow cell 20, the flow cell 20 provides a flow layer that ranges from 0.1 mm to 2 mm, and preferably from 0.5 mm to 1 mm. Evaluation of transmission color is generally avoided in the present invention and evaluation of the reflection color employed because the latter more accurately characterizes of the hues and shades exhibited by effect pigments.

A pump (not shown) advances the pigment dispersion 22 to the flow cell 20 from either a reaction flask or a reactor (not shown). The flow rate through the flow cell 20 is adjusted to appropriately flush the flow cell 20 completely with the pigment dispersion 22 and minimize cavitation.

During the process of forming the pigment, a substrate, such as mica, is coated with a high refractive index material, generating an interference color. To evaluate the coating process and the interference color, an aliquot of the dispersion of in-process platy effect pigment is pumped through the flow cell 20. Light 30 emitted from an emitter 32 reflects off of the pigment dispersion 22. The color of the reflected light 34 is measured at predetermined time intervals. When the reflected light color matches the reflected light characteristics of a selected dispersion standard, the coating process is halted.

Color matching can be accomplished by wavelength, dominant wavelength, or color space parameters, such as those prescribed by CIELab, etc. Once the pigment achieves a color match with a selected standard, the reactor can be shut down, and the process halted automatically without the need for human intervention.

The following examples are illustrative, but not limiting, of the invention:

EXAMPLE 1

A slurry of glass platelets in a morton flask was titrated with a solution of $TiOCl_2$ and NaOH such that a hydrated $TiO_2$ layer formed on the borosilicate platelets which generated an interference color. As the film developed, the slurry periodically was pumped through a flow cell, measuring 5×5.5×0.1 cm, with a peristaltic pump at approximately 200 ml/min.

The flow cell was mounted on a goniospectrophotometer. The goniospectrophotometer measured the color of light reflected off of a first target slurry to determine the desired endpoint color. Measurements were taken at 25 degrees from the specular angle.

Figure 2:
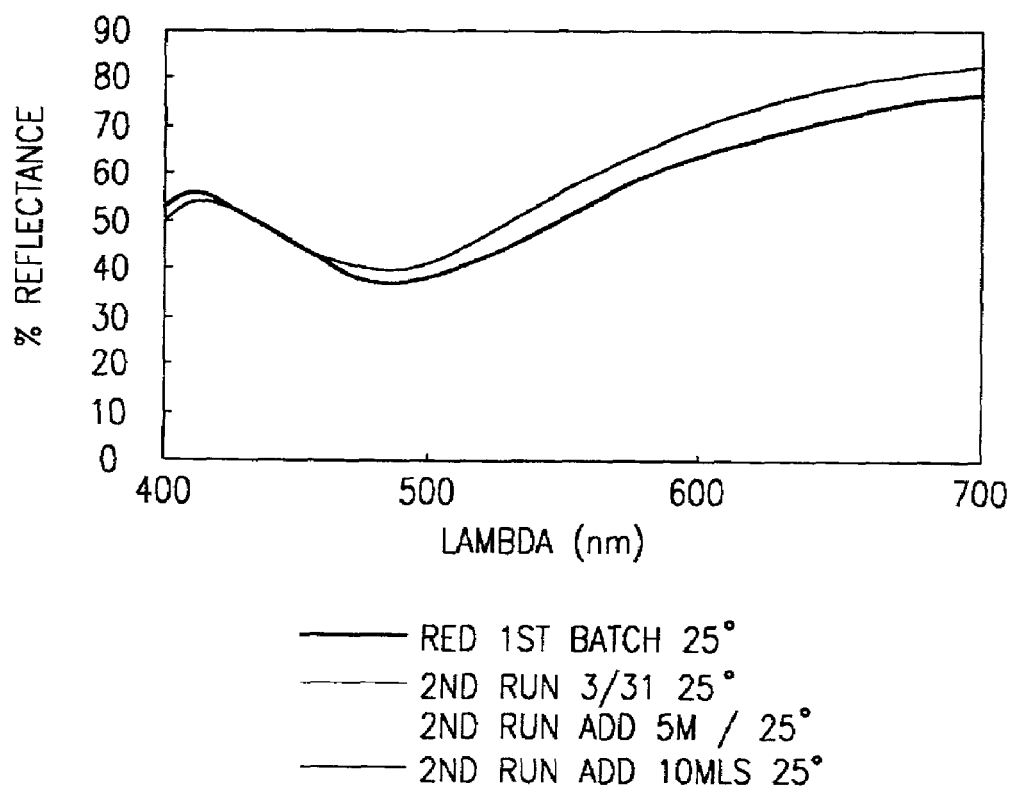

The goniospectrophotometer measured the color of samples during a second coating run at different stages of the coating process. A color match was established for each sample based on $L_{min}$. FIG. 2 shows the spectra of the slurries measured with the flow cell. When the first and second slurry colors matched, the coating process was stopped, and the sample was washed, filtered and calcined to yield a good color match to the desired color.

EXAMPLE 2

The slurry of this example was similar to that in example 1, except that the slurry included mica coated with hydrated $TiO_2$. First, a red $TiO_2$ coated mica effect pigment was measured and established as the standard. Additional samples were evaluated during the coating of a second mica batch. Color data generated from the flow cell system indicated completion of the reaction. The samples were processed further to produce a good color match.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

We claim:

1. Method for continuously controlling color of an interference effect pigment during the pigment preparation comprising coating a platy substrate with a hydrous layer to form a pigment, providing a flow cell with an oriented sample of said pigment being formed, impinging light on said sample, comparing a characteristic of light reflected from said sample of the pigment with a standard, and terminating said coating when the characteristic corresponds with the standard.

2. Method of claim 1, wherein the characteristic is a characteristic of an interference effect of light reflected from the pigment.

3. Method of claim 1, wherein said comparing a characteristic of light comprises comparing wavelength, dominant wavelength, color space parameters or a combination thereof.

4. Method of claim 1, wherein said ample comprises mica coated with high refractive index material.

5. Method of claim 1, wherein said flow cell is a thin layer flow cell and the method further comprises providing a sample of the pigment being formed to said flow cell.

* * * * *